(12) United States Patent
Shener-Irmakoglu

(10) Patent No.: US 10,864,010 B2
(45) Date of Patent: Dec. 15, 2020

(54) SURGICAL HANDPIECE AND LATCHING HUB SYSTEM

(71) Applicant: Smith & Nephew, Inc., Memphis, TN (US)

(72) Inventor: Cemal Shener-Irmakoglu, Woburn, MA (US)

(73) Assignee: SMITH & NEPHEW, INC., Memphis, TN (US)

( * ) Notice: Subject to any disclaimer, the term of this patent is extended or adjusted under 35 U.S.C. 154(b) by 266 days.

(21) Appl. No.: 16/086,677

(22) PCT Filed: Apr. 11, 2017

(86) PCT No.: PCT/US2017/027006
§ 371 (c)(1),
(2) Date: Sep. 20, 2018

(87) PCT Pub. No.: WO2017/180622
PCT Pub. Date: Oct. 19, 2017

(65) Prior Publication Data
US 2019/0110807 A1 Apr. 18, 2019

Related U.S. Application Data

(60) Provisional application No. 62/322,464, filed on Apr. 14, 2016.

(51) Int. Cl.
*A61B 17/32* (2006.01)
*A61B 17/00* (2006.01)
*A61B 17/16* (2006.01)

(52) U.S. Cl.
CPC .... *A61B 17/32002* (2013.01); *A61B 17/1644* (2013.01); *A61B 17/1659* (2013.01); *A61B 2017/00477* (2013.01); *A61B 2017/1602* (2013.01); *A61B 2217/005* (2013.01); *A61B 2217/007* (2013.01)

(58) Field of Classification Search
CPC ... A61B 17/32; A61B 17/16; A61B 17/32002; A61B 2017/00477; A61B 2017/1602; A61B 17/1644; A61B 17/1659; A61B 2217/005; A61B 2217/007
See application file for complete search history.

(56) References Cited

U.S. PATENT DOCUMENTS 5,376,078 A 12/1994 Dinger, III et al.
6,066,152 A 5/2000 Strauss et al.
(Continued)

FOREIGN PATENT DOCUMENTS

EP 2815705 A1 12/2014
WO 2015/112938 A1 7/2015
WO 2016/022790 A1 2/2016

OTHER PUBLICATIONS

European Patent Office, Office Action in corresponding European application (17720643), dated Mar. 20, 2020; 5 pages.
(Continued)

*Primary Examiner* — George J Ulsh

(57) ABSTRACT

Example embodiments include a drive unit and a hub and cutting implement that may be coupled to the hub by use of a latch between the hub and the drive unit. The latch may be configured to couple with the drive unit at locations on the perimeter of the drive unit. Some embodiments of the invention also include one or both of resection controls and fluid management systems.

17 Claims, 10 Drawing Sheets

(56) References Cited

U.S. PATENT DOCUMENTS

| | | |
|---|---|---|
| 2002/0151902 A1 | 10/2002 | Riedel et al. |
| 2012/0029354 A1 | 2/2012 | Mark et al. |
| 2012/0259337 A1 | 10/2012 | del Rio et al. |
| 2015/0133983 A1 | 5/2015 | Loreth |
| 2016/0030057 A1 | 2/2016 | Loreth et al. |
| 2016/0095613 A1 | 4/2016 | Trondle |
| 2016/0120586 A1 | 5/2016 | Spycher et al. |

OTHER PUBLICATIONS

European Patent Office, Office Action in corresponding European application (17720643), dated Aug. 30, 2019; 6 pages.
European Application No. 17720643.0-1113 Examination Report dated Aug. 30, 2019.
International Search Report dated Jul. 27, 2017 for PCT application No. PCT/US2017/027006 filed Apr. 11, 2017; 8 pages.
Written Opinion dated Jul. 27, 2017 or PCT application No. PCT/US2017/027006 filed Apr. 11, 2017; 9 pages.

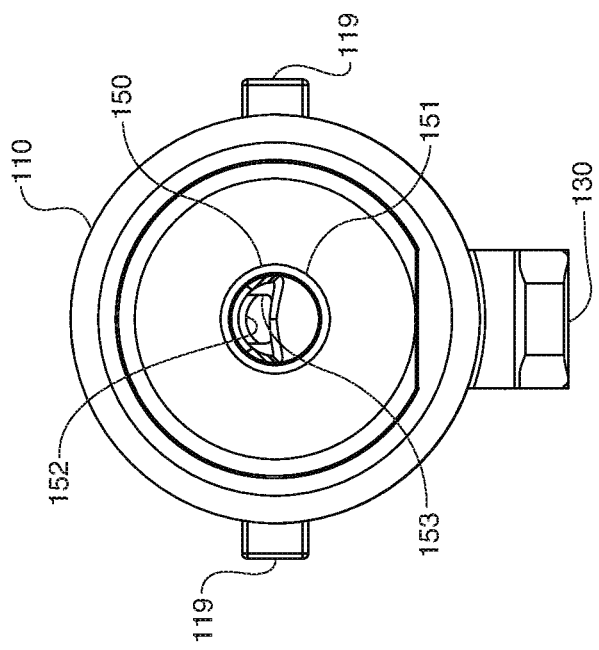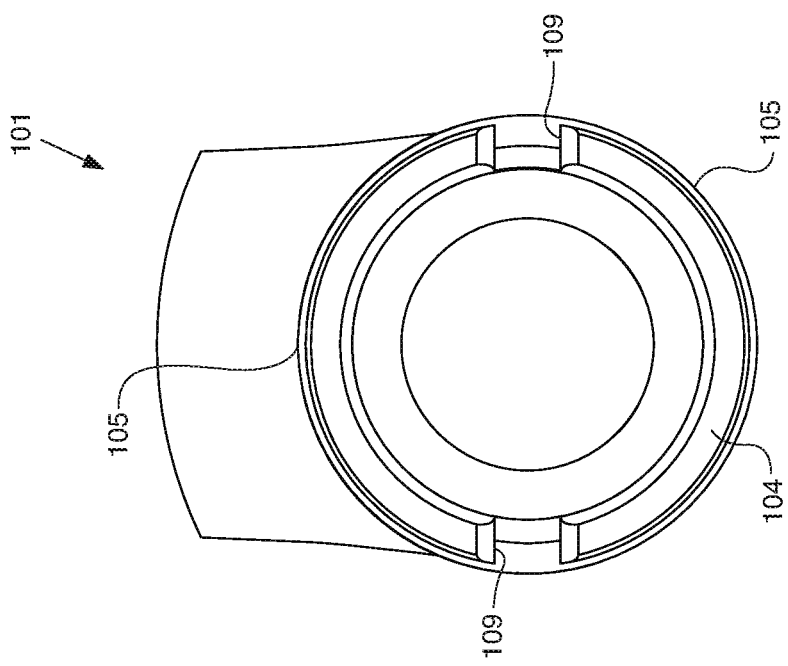

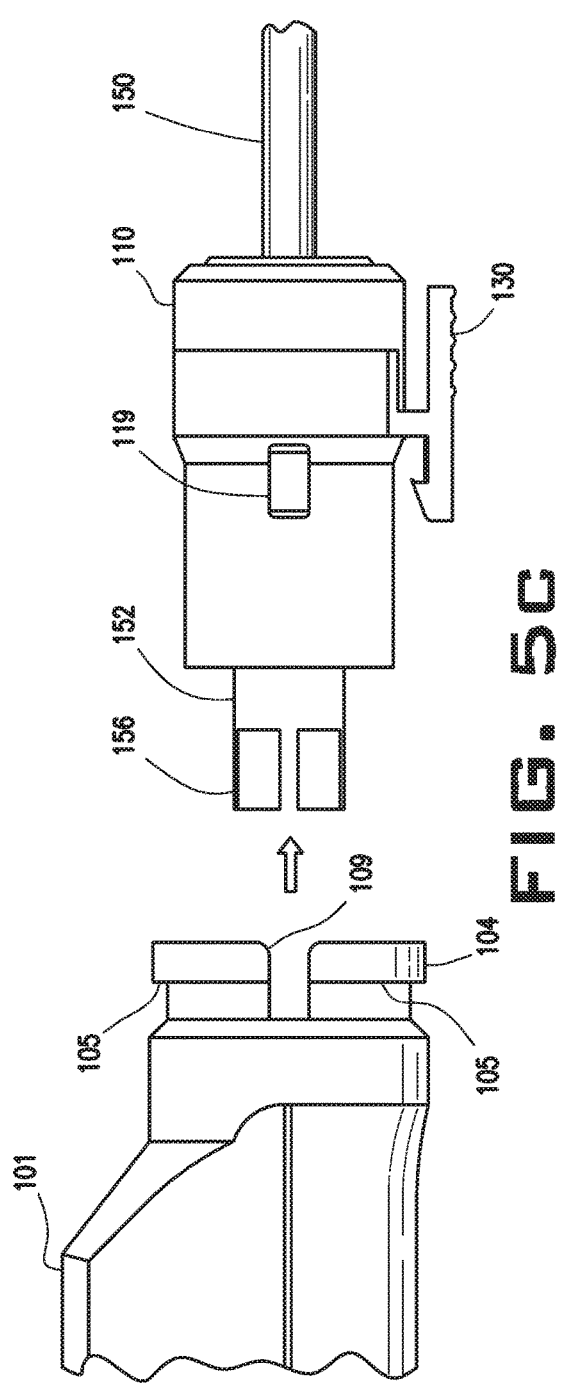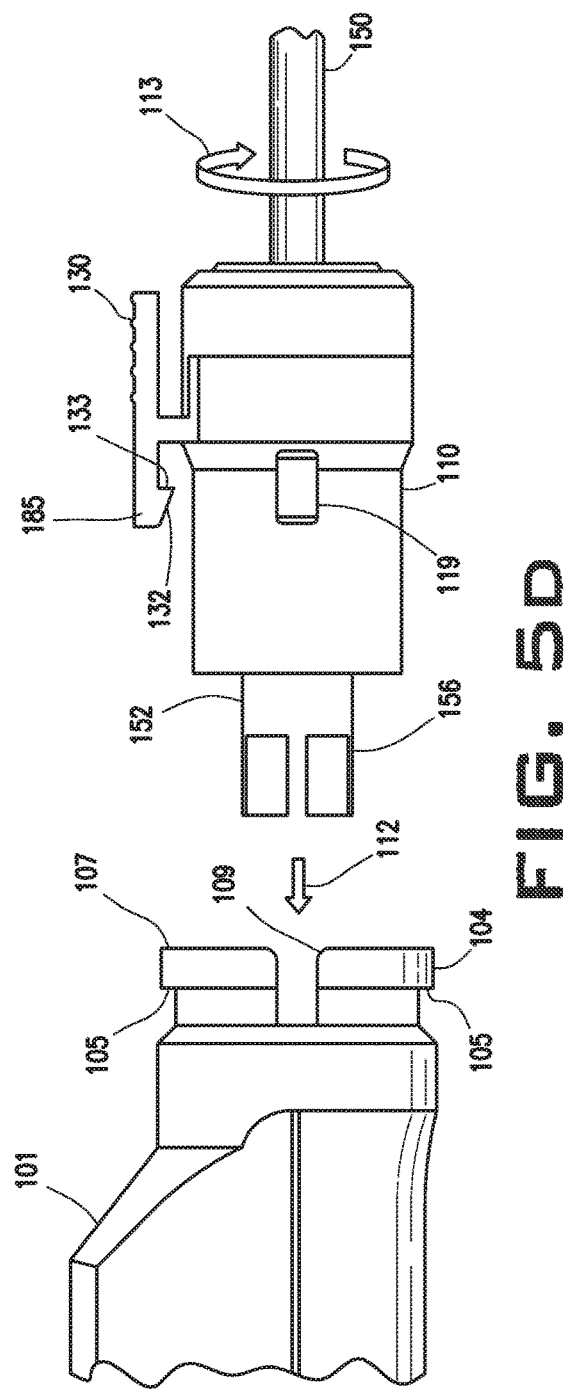

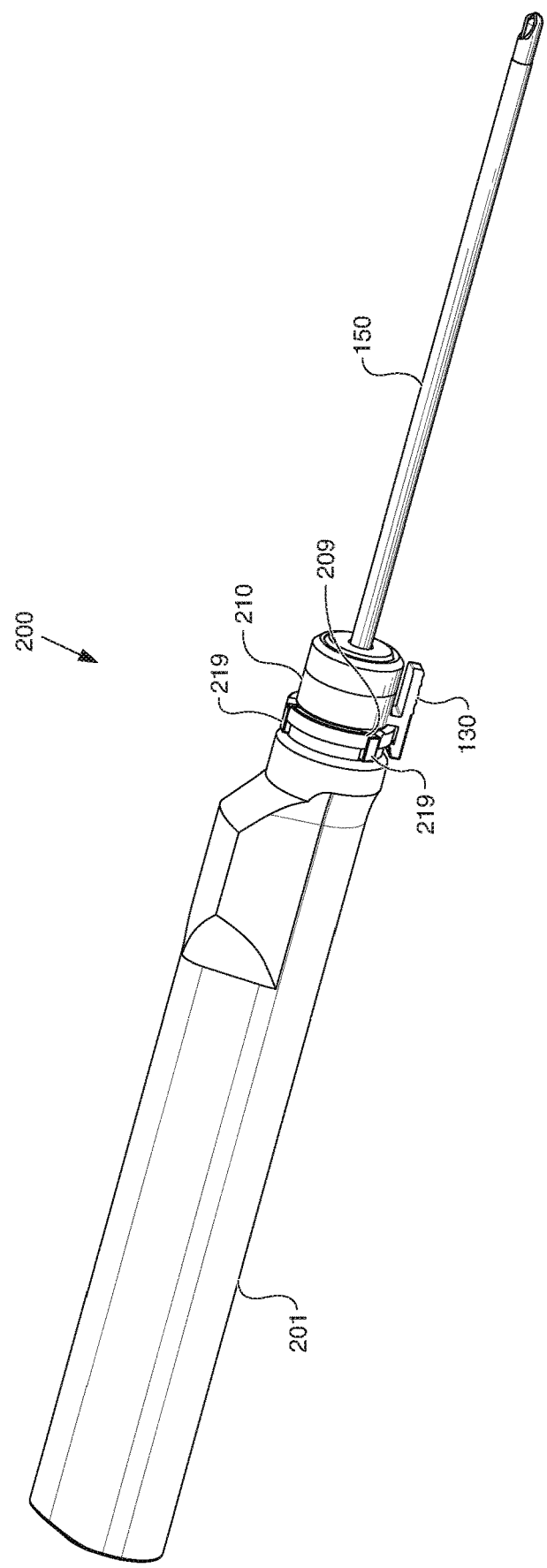

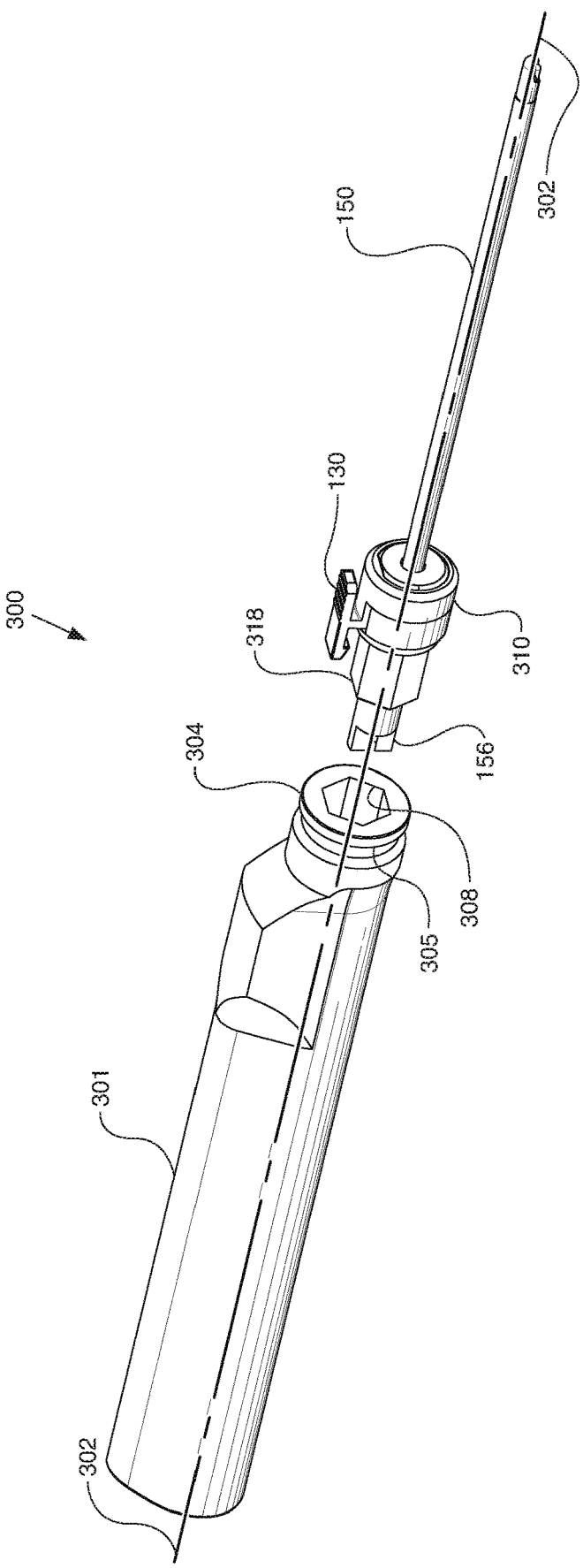

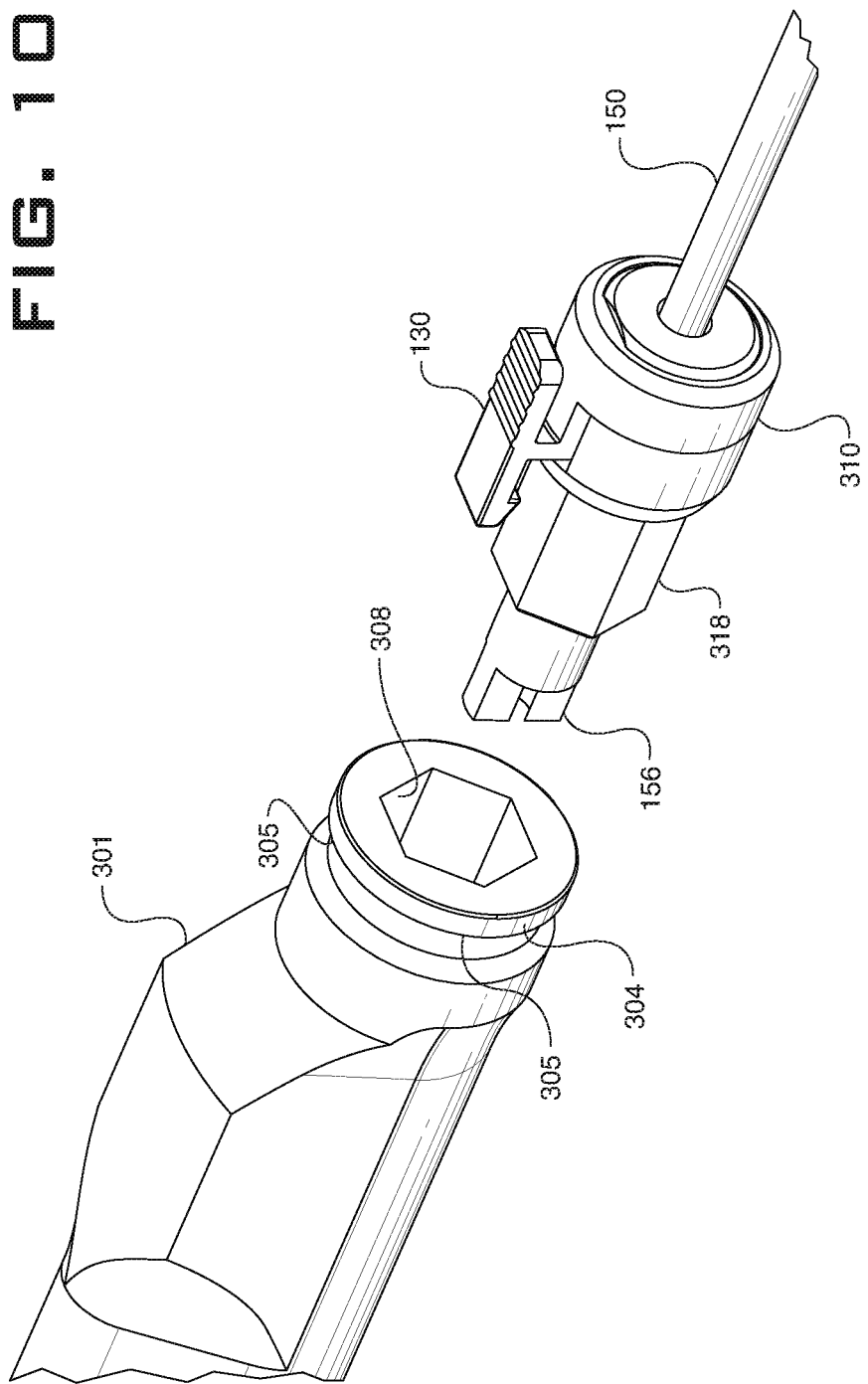

SURGICAL HANDPIECE AND LATCHING HUB SYSTEM

CROSS-REFERENCE TO RELATED APPLICATIONS

This application is a U.S. National Phase Entry of PCT application serial no. PCT/US2017/027006 filed Apr. 11, 2017 and titled "Surgical Handpiece and Latching Hub System." The PCT application claims the benefit of U.S. Provisional Application Ser. No. 62/322,464 filed Apr. 14, 2016 titled "Surgical Handpiece and Latching Hub System." Both applications are incorporated by reference herein as if reproduced in full below.

FIELD

The various embodiments relate to the field of surgical instruments, and more particularly relates to interconnections among components of surgical cutting instruments such as blades or burrs used in endoscopic surgery to cut tissue. Some embodiments include fluid management and resection control components in combination with cutting instruments.

BACKGROUND

Surgical cutting devices with drive units are commonplace in endoscopic surgery. It is typical for such surgical cutting devices to include a motorized drive unit, sometimes also referred to as a handpiece, and to include a cutting implement with a hub. One of the challenges associated with such instruments is to provide a secure removable coupling between a drive unit and a hub that is both simple to attach and remove and readily accessible for cleaning. One of the complications with couplings of related-art devices is that latching or other securing mechanisms are located within components of the surgical instruments and are therefore harder to access, operate, and clean.

SUMMARY

An example embodiment is a system comprising a drive unit and a cutting implement. The drive unit may comprise: a longitudinal axis; a perimeter about a cross-section of the drive unit transverse to the longitudinal axis, the perimeter at distal end of the drive unit; an annular groove disposed proximally of the perimeter on an outside surface of the drive unit; and an opening at the distal end of the drive unit, the opening defines an internal volume with an inside surface. The cutting implement may comprise: a hub telescoped within the internal volume, an outside surface of the hub abuts the inside surface of the opening; a latch disposed on the outside surface of the hub, the latch comprising an engaging member releasably coupled to the annular groove; an outer tube coupled to the hub; and a cutter near a distal tip of the outer tube.

Another embodiment is a cutting implement that comprises: a hub that defines an outside surface; an outer tube rigidly coupled to the hub, the outer tube defines a longitudinal axis; an inner tube telescoped with the outer tube along the longitudinal axis; a first protrusion that extends radially outward from the hub; a latch disposed on the outside surface of the hub, the latch comprising an engaging member on an inside surface of the latch; and a cutter defined at the distal end of the outer tube and inner tube.

An embodiment is a method comprising: telescoping a hub of a cutting implement into an opening at a distal end of a drive unit; latching the cutting implement to an annular groove defined on an outside surface of the distal end of the drive unit, the latching by a latch disposed on an outside surface of the hub; and resecting tissue with the cutting implement and drive unit.

Another embodiment is a cutting tool that includes a drive unit with a longitudinal axis and a perimeter about a cross-section of the drive unit transverse to the longitudinal axis. Some embodiments include multiple latch receiving locations about the perimeter. The embodiment also includes a hub configured to releasably couple with the drive unit and a latch configured to releasably couple between the hub and at least one of the multiple latch receiving locations. A cutting implement may be coupled with the hub that includes a cutter near a distal tip of the cutting implement.

Another embodiment is a cutting tool with a drive unit and a hub configured to releasably couple with the drive unit, wherein the hub includes a latch with an engaging member that, when the hub is seated in the drive unit, is movable from a first position that does secure the hub relative to the drive unit to a second position that does not secure the hub relative to the drive unit, and wherein the latch extends around an exterior portion of the drive unit when the hub is seated in the drive unit. A cutting implement may be coupled with the hub that includes a cutter near a distal tip of the cutting implement.

Yet another embodiment is a cutting tool that includes a drive unit with a perimeter groove near a distal end of the drive unit and a hub radially lockable at two or more discrete radial orientations relative to the drive unit, wherein the hub includes a latch that is configured to secure the hub longitudinally relative to the drive unit by engaging the perimeter groove near a distal end of the drive unit at any radial orientation when the hub is seated in the drive unit. A cutting implement may be coupled with the hub that includes a cutter near a distal tip of the cutting implement.

Still another embodiment is a system for cutting that includes a cutting tool, a resection control, and a fluid management system. Embodiments of the cutting tool of the system include a drive unit with a longitudinal axis and a perimeter about a cross-section of the drive unit transverse to the longitudinal axis, wherein there are multiple latch receiving locations about the perimeter, a hub configured to releasably couple with the drive unit, a latch configured to releasably couple between the hub and at least one of the multiple latch receiving locations, and a cutting implement coupled with the hub that includes a cutter near a distal tip of the cutting implement. The resection control may be electrically coupled to the cutting tool, and the fluid management system of some embodiments includes a pump control and a fluid passage between the pump control and the cutting tool.

BRIEF DESCRIPTION OF THE DRAWINGS

FIG. 3 is a distal end elevation view of a drive unit of the cutting tool of FIG. 1.

FIG. 4 is a distal end elevation view of a hub and a cutting implement of the cutting tool of FIG. 1.

FIG. 5C is a side elevation view of the hub and the distal end of the drive unit of FIG. 5A showing the hub after being moved away from the drive unit.

FIG. 5D is a side elevation view of the hub and the distal end of the drive unit of FIG. 5A after the hub has been rotated about its longitudinal axis approximately one-half of a revolution and is positioned to be coupled with the drive unit.

FIG. 6 is a perspective view of an embodiment of a cutting tool.

FIG. 9 is a partially exploded perspective view of another embodiment of a cutting tool.

FIG. 10 is an enlarged partially exploded perspective view of portions of the cutting tool of FIG. 9.

DEFINITIONS

Figure 1:
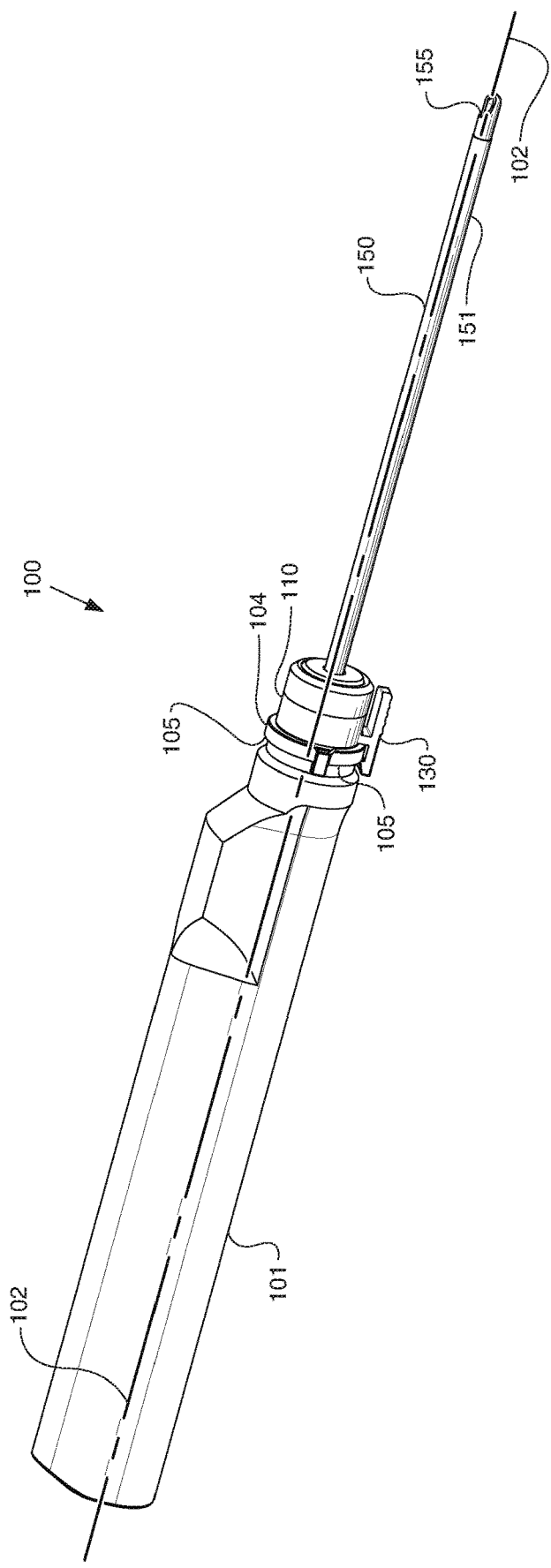
FIG. 1 is a perspective view of an embodiment of a cutting tool.

For the following discussion and claims, the terms "including" and "comprising" are used in an open-ended fashion, and thus should be interpreted to mean "including, but not limited to . . . ." Also, the term "couple" or "couples" is intended to mean either a direct or indirect connection. Thus, if a first device couples to a second device, that connection may be through a direct connection or through an indirect connection via other devices and connections.

"Circular" in relation to the perimeter of the distal end of the drive unit shall mean that circumference (conceptually carried across notches) of the perimeter is circular. Stated otherwise, the absence of portions of the perimeter given the presence of notches shall not obviate that the perimeter is circular.

"Releasably coupled" shall mean that first device is coupled to a second device, and the first device can be de-coupled from a second device without cutting, breaking, disabling, damaging, or destroying either the first or second device.

DETAILED DESCRIPTION

A system for cutting with a cutting tool 100, 200, 300 and their respective component parts are illustrated in FIGS. 1-11. As used herein the term "cutting tool" may include not only tools that cut with a blade but tools that abrade, scratch, rub, dislodge, or otherwise manipulate tissue. An embodiment of the cutting tool 100 is illustrated in FIGS. 1-5D that includes a drive unit 101, and a cutting implement 150 that comprises a hub 110, and a latch 130, outer tube 151, and inner tube 152. The drive unit 101 may be a motorized drive unit powered by an electric motor and a battery, transformer, capacitor, wire, or other source of electricity, may be powered by air pressure or other fluid pressure, may be powered by manual or automated user manipulation, or may be powered by any other effective mechanism. The drive unit 101 may include any effective set controls for dictating the function of the drive unit 101. The set of controls may include buttons, switches, sliders, indicators, and other mechanisms or displays to adjust and control functions of the drive unit 101. For example and without limitation, the controls may be used to one or more of power the drive unit 101 on and off, set a rotating speed for a portion of the drive unit 101, activate a clockwise or counterclockwise rotation of a portion of the drive unit, indicate a status or function of the drive unit 101, and provide any other useful control or display associated with the drive unit 101. Function and control may also be accomplished by use of a control system coupled with the drive unit 101, and may further include use of separate controls such as foot operated controls.

The drive unit 101 depicted in FIG. 1 includes a longitudinal axis 102 and a perimeter, where the perimeter extends about a cross-section of the drive unit 101 transverse to the longitudinal axis 102 at the distal end of the drive unit 101. In example systems, a cross-section of the perimeter of the drive unit 101 is substantially circular; however, no specific perimeter cross-sectional shape is required to be within the scope of the various embodiments. An annular groove 105 is disposed on an outside surface at the distal end of the drive unit 101, the annular groove 105 disposed proximally of the perimeter. The annular groove 105 defines multiple latch receiving locations about the perimeter of the drive unit 101 depicted in FIGS. 1-3 and 5A-5D. The annular groove 105 of the illustrated embodiment is formed by a circular flange or rim 104, and the rim 104 defines the perimeter with the example circular cross-section of the drive unit 101. The annular groove 105 provides substantially continuous latch receiving locations about the perimeter of the drive unit 101.

The hub 110 of the illustrated embodiment is configured to releasably couple with the drive unit 101. In particular, the drive unit 101 defines an opening 199 at the distal end 197 of the drive unit 101. The opening 199 defines an internal volume 195 with an inside surface 193. When the drive unit 101 is coupled to the cutting implement 150, the hub 110 is telescoped within the internal volume 195 such that an outside surface 191 of the hub 110 abuts the inside surface 193 of the opening 199.

The latch 130 depicted in FIGS. 1, 2, 4, and 5A-5D is configured to releasably couple between the hub 110 and at least one of the multiple latch receiving locations in the form of the annular groove 105 of the drive unit 101. In the embodiment illustrated, the latch 130 is fixed to the outside surface 191 of the hub 110 (and in the examples shown, the latch 130 is disposed between two protrusions along the circumference of the outside surface of the hub). In the example system, hinge point of the latch 130 disposed distally from the protrusions. The hub 110 is configured to releasably couple with the drive unit 101. Referring to FIGS. 5A-5D, the latch 130 defines a hinge 189 that defines a rotational axis 187. In the view of FIGS. 5A-5D, the rotational axis 187 is perpendicular to the plane of the page, and thus the rotational axis 187 is shown as a dot. However, the rotational axis 187, projected onto the longitudinal axis of the drive unit 101, is perpendicular to the longitudinal axis. Moreover, and as shown, the rotational axis 187 is either tangent to the outer surface 191 of the hub 110, or is parallel to a tangent to the outer surface of the hub 110, depending on the type of hinge used.

In other embodiments, a latch may be fixed to a drive unit and configured to releasably couple with a hub. Any effective mechanism or structure capable of restricting longitudinal separation of a hub and the drive unit when in a first position of the latch, and permitting longitudinal separation of a hub and a drive unit in a second position, may be a "latch" as that term is used herein.

As illustrated in FIGS. 5A-5D, the hub 110 may be released from the drive unit 101 by pressing the latch 130 in the direction of arrow 111 (FIG. 5B) to move or rotate the latch to the latch's second position and separating the hub 110 from the drive unit 101. That is, the example latch 130 comprises a first cantilever portion 185 and a second cantilever portion 183 on the opposite side of the latch from the hinge 189. The first cantilever portion 185 protrudes proximally from the hinge 189, and the second cantilever portion 183 extends distally from the hinge 189. An inside surface of the first cantilever portion 185 comprises sloped or chamfered leading edge 132 on the proximal end of the first cantilever portion 185, as well as the shoulder region or engaging member 133 in operational relationship to the chamfered leading edge 132. The chamfered leading edge 132 and engaging member 133 are configured such that when the hub 110 is moved proximally along the longitudinal axis of the drive unit 101, the latch 130 is forced into a position where the engaging member 133 couples to the annular groove 105.

More particularly, the latch 130 is positioned on the hub 110 such that when the hub 110 is moved proximally along the longitudinal axis 102 to couple with the drive unit 101, the latch 130 is forced into the first position that secures the hub 110 (FIG. 5A) relative to the drive unit 101 on at least one of the latch receiving locations defined by annular groove 105 of the drive unit 101. The latch 130 of the illustrated embodiment includes a chamfered leading edge 132 (FIG. 5D) that when moved in the direction of an arrow 112 will contact a distal edge 107 of the drive unit 101. The incline of the chamfered leading edge 132 contacting the distal edge 107 causes the latch 130 to pivot about hinge 189, similar to the pivot illustrated in FIG. 5B. The example latch 130 includes a living hinge that enables pivoting about the rotational axis 187. However, in other embodiments, hinge action may be achieved with a pin and spring combination or any other effective mechanism or structure. When the latch 130 is moved in the direction of the arrow 112 into one of the latch receiving locations in the form of annular groove 105 of the drive unit 101, the latch 130 may be described as "snapping" into place in the groove 105. The latch 130 includes an engaging member 133 (FIG. 5D) that, when the hub 110 is seated in the drive unit 101, is movable from the second position (FIG. 5B) that does not secure the hub 110 relative to the drive unit 101 to the first position (FIG. 5A) that does secure the hub 110 relative to the drive unit 101. The engaging member 133 effectively forms a hook, but in other embodiments, engaging members may include any effective securing structure, including but limited to a pin, a wedge, a key, or a thread. As illustrated in each embodiment herein, the latch 130 extends partially around an exterior portion of the drive unit 101, 201, 301 when the hub 110, 210, 310 is telescoped within the drive unit 101, 201, 301. With the latch 130 in the first position, the hub 110, 210, 310 may be described as being longitudinally and radially locked at two, three, and six discrete radial orientations respectively relative to the drive unit 101, 201, 301.

Figure 5A:
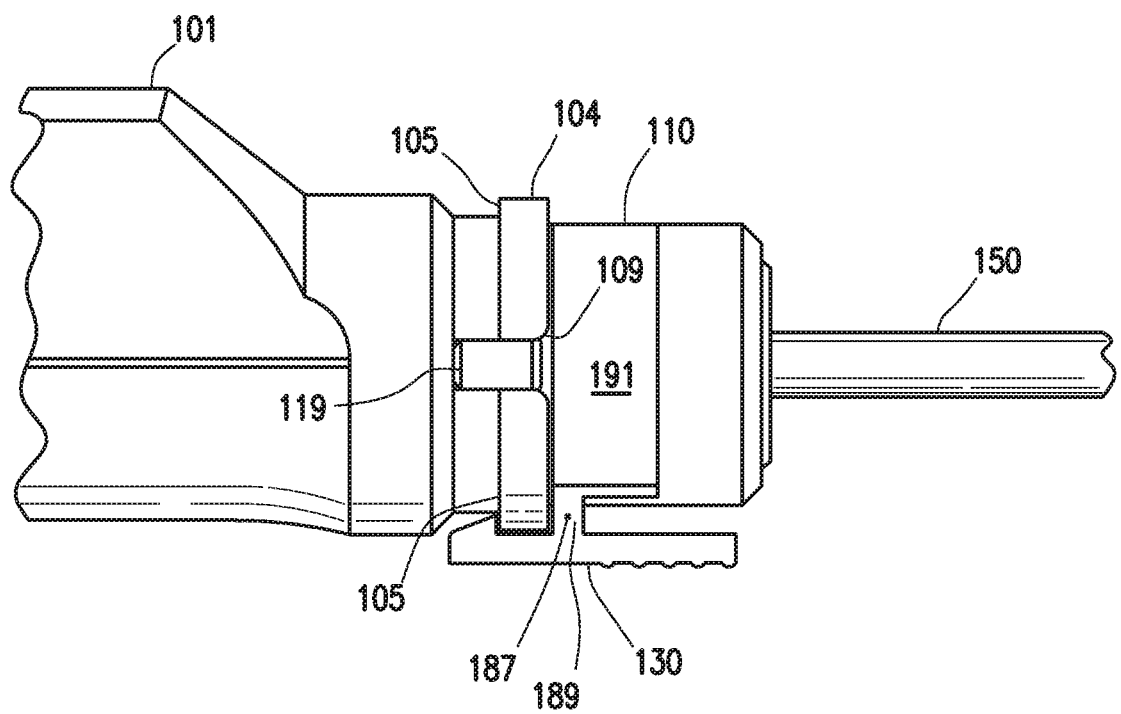
FIG. 5A is a side elevation view of a hub and a distal end of a drive unit of the cutting tool of FIG. 1 with the hub seated in the drive unit.
Figure 5B:
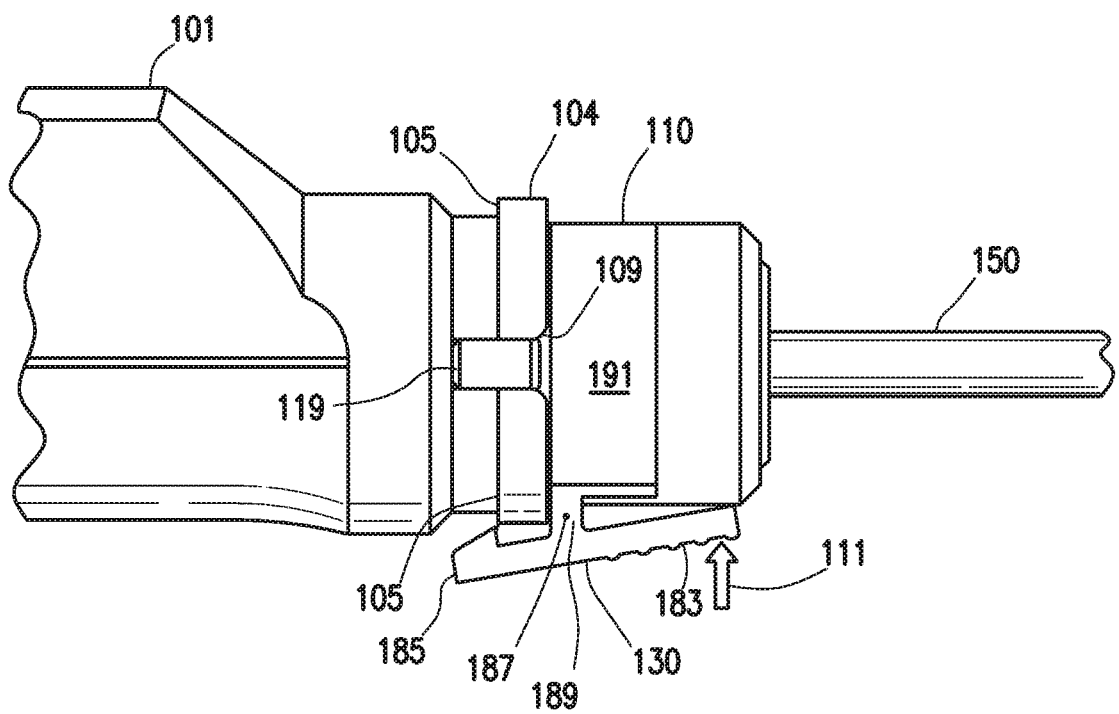
FIG. 5B is a side elevation view of the hub and the distal end of the drive unit of FIG. 5A showing a latch after being moved to a second position that does not secure the hub relative to the drive unit.
Figure 8:
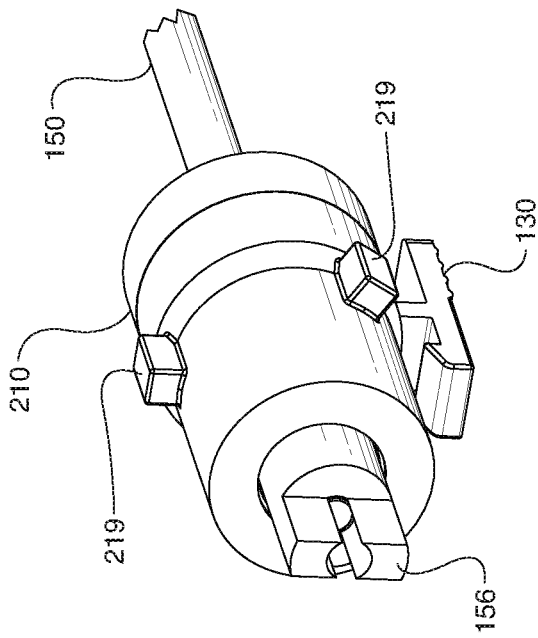
FIG. 8 is a perspective view of a proximal portion of a hub and cutting implement of the cutting tool of FIG. 6.
Figure 7:
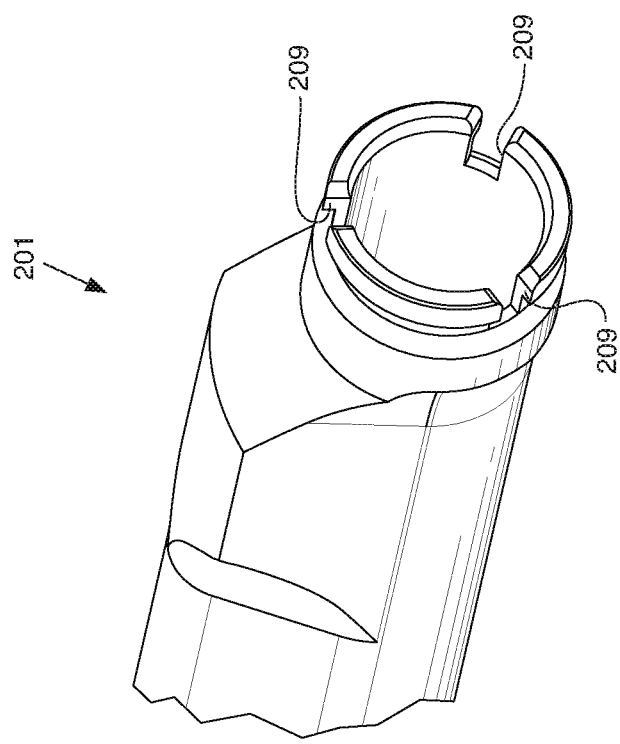
FIG. 7 is a perspective view of a distal portion of a drive unit of the cutting tool of FIG. 6.

The example drive unit 101 of the cutting tool 100 includes two slots 109 (FIGS. 2, 3, and 5A-5D) open on the distal end of the drive unit 101. The example hub 110 includes two protrusions 119 (FIGS. 2, 4, and 5A-5D). The protrusions 119 extend radially outward from the outer surface 191 of the hub 110 and are configured to be rotationally aligned (relative to the longitudinal axis 102) with and telescoped in the slots 109 of the drive unit 101. As shown in FIGS. 5A and 5B, the protrusions 119 may be telescoped or seated in the slots 109 in the drive unit 101 to orient the hub 110 of the cutting implement 150 relative to the drive unit 101. As illustrated by the different orientations between FIGS. 5C and 5D, the example two protrusions 119 are configured to be aligned, telescoped, and seated in the two slots 109 in the drive unit 101 in two different orientations that orient the hub 110 of the cutting implement 150 in two different orientations relative to the drive unit 101. Consequently, the hub 110 may be positioned at two discrete radial orientations relative to the drive unit 101 when the hub 110 is fully seated in the drive unit 101. As depicted by an arrow 113 in FIG. 5D, the relative orientation of the hub 110 and the cutting implement 150 has been changed by one-half of a rotation from the orientation of FIGS. 5A-5C so that a second orientation may be achieved without substituting the instruments being used.

Another embodiment of a cutting tool, cutting tool 200, is illustrated in FIG. 6. A drive unit 201 of the cutting tool 200 embodiment includes three slots 209 open on the distal end of the drive unit 101 (FIGS. 6 and 7; two of three slots 209 are visible in FIG. 6). Example hub 210 includes three protrusions 219 extending radially outward from the outer surface of the hub 210 (FIGS. 6 and 8; two of three protrusions 219 are visible) configured to be rotationally aligned (relative to the longitudinal axis 102) with and telescoped in the three slots 209 of the drive unit 201. The cutting tool 200 also includes an implementation of the latch 130 fixed to the outside surface of the hub 210. The protrusions 219 may be seated in the three slots 209 in the drive unit 201 to orient the hub 210 of the cutting implement 150 relative to the drive unit 201. The three protrusions 219 are configured to be aligned, telescoped, and seated in the three slots 209 in the drive unit 201 in three different orientations that orient the hub 210 of the cutting implement 150 in three different orientations relative to the drive unit 201. Consequently, the hub 210 may be positioned at three discrete radial orientations relative to the drive unit 201 when the hub 210 is fully seated in the drive unit 201. The relative orientation of the hub 210 of the cutting implement 150 may be changed by one-third of a rotation without substituting the instruments being used.

Other embodiments of a drive unit may include any number of slots or other mating features to provide for alternative orientations of a cutting implement with a drive unit. Some embodiments may include a lesser but complimentary number of protrusions than slots. For example, either of the drive units 101, 201 may be coupled with a hub that has only one protrusion and a desired alignment may be achieved when the hub is seated in the drive unit 101, 201. By way of another example, the drive unit 201 may be coupled with a hub that has two protrusions approximately 120 degrees apart and a desired alignment may be achieved when the hub is seated in the drive unit 201. Considered more generally, an equal number of slots and protrusions X degrees apart (where 360 is divisible by X with no remainder) will make possible 360 divided by X possible different relative orientations of a hub and a drive unit. Releasable coupling between the drive unit 201 and the hub 210 with the latch 130 is essentially similar to the releasable coupling described in connection with the drive unit 101 and hub 110 and will not be additionally described here so as not to unduly complicate the disclosure.

A cutting tool 300 is illustrated in FIGS. 9 and 10 with a drive unit 301 that includes an angularly sided opening 308 near a distal end of the drive unit 301. In the illustrated embodiment, the angularly sided opening 308 has six sides of equal length. However, in other embodiments, the number of sides may be larger or smaller than six and the lengths of each side may or may not be equal.

The cutting tool 300 depicted also includes a hub 310, an implementation of the latch 130 fixed to the hub 310 of the cutting implement 150 coupled with the hub 310. The hub 310 shown in FIGS. 9 and 10 includes an angularly sided proximal connector 318 configured to be aligned and seated in the angularly sided opening 308. The angularly sided proximal connector 318 shown has six sides of equal length, but other embodiments may have a larger or smaller number of sides and each side may or may not be of equal length. For example, an angularly sided proximal connector of some embodiments may include four sides. Such a four-sided connector may fit within a four-sided opening, may fit within a six-sided opening such as the angularly sided opening 308, or may fit within any opening with which the connector cooperates.

The angularly sided proximal connector 318 may be seated in the angularly sided opening 308 to orient the hub 310 of the cutting implement 150 relative to the drive unit 301. The angularly sided proximal connector 318 and the angularly sided opening 308 are configured to be aligned and seated together in six different orientations that orient the hub 310 of the cutting implement 150 in six different orientations relative to the drive unit 301. Consequently, the hub 310 may be positioned at six discrete radial orientations relative to the drive unit 301 when the hub 310 is fully seated in the drive unit 301. Similarly, other cooperating shapes of proximal connectors and openings may be used to provide different numbers and increments of relative orientations.

The drive unit 301 depicted in FIG. 9 includes a longitudinal axis 302 and a perimeter, where the perimeter extends about a cross-section of the drive unit 301 transverse to the longitudinal axis 302 at the distal end of the drive unit 301. A cross-section of the perimeter along some portions of the drive unit 301 is substantially circular, but at other portions is irregularly shaped. No specific perimeter cross-sectional shape is required to be within the scope of the various embodiments. There are multiple latch receiving locations in the form of annular groove 305 about the perimeter of the drive unit 301 depicted in FIGS. 9 and 10. The latch receiving locations in the form of annular groove 305 of the illustrated embodiment are formed by a flange or rim 304 in combination with a generally circular cross-section of the drive unit 301. The resulting structure provides substantially continuous latch receiving locations about the perimeter of the drive unit 301.

The hub 310 of the illustrated embodiment is configured to releasably couple with the drive unit 301 at the orientations noted above for the angularly sided proximal connector 318 and the angularly sided opening 308. The latch 130 depicted in FIGS. 9 and 10 is configured to releasably couple between the hub 310 and at least one of the multiple latch receiving locations of the drive unit 301. In the embodiment illustrated, the latch 130 is fixed to the hub 310 and configured to releasably couple with the drive unit 301. In other embodiments, a latch may be fixed to a drive unit and configured to releasably couple with a hub. Any effective mechanism or structure capable of restricting longitudinal separation of a hub and the drive unit when in a first position and permitting longitudinal separation of a hub and a drive unit in a second position may be a "latch" as that term is used herein. As illustrated in FIGS. 9 and 10, the latch 130 is positioned on the hub 310 such that when the hub 310 is moved proximally along the longitudinal axis 302 of the drive unit 301 to couple with the drive unit 301, the latch 130 is forced into a position that secures the hub 310 relative to the drive unit 301 on at least one of the latch receiving locations of the drive unit 301. The latch 130 of the illustrated embodiment includes the same structure as described in association with FIGS. 1-5D herein and will not be additionally described here so as not to unduly complicate the disclosure.

Figure 2:
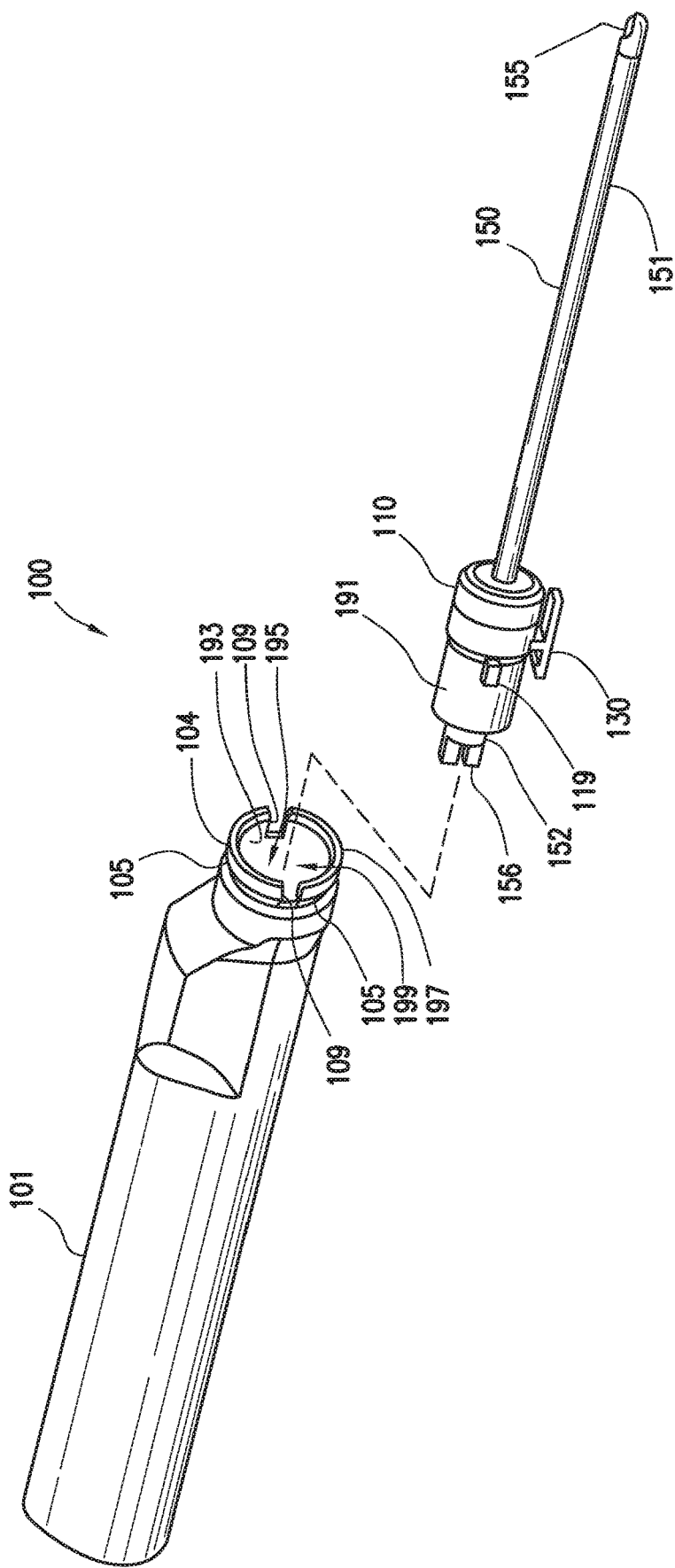
FIG. 2 is a partially exploded perspective view of the cutting tool of FIG. 1 with components rotated to different perspectives to show features of the components.

The cutting implement 150 as shown includes the hub 110, 210, 310. The cutting implement 150 shown in FIG. 4 includes an outer tube or outer tubular member 151 and an inner tubular member 152 that has a cutter 153 near a distal tip of the cutting implement 150. The example cutter 153 is part of the inner tubular member 152 and is configured to rotate relative to the outer tubular member 151. The outer tubular member 151 shown is rotationally fixed relative to the hub 110, 210, 310. As illustrated in FIGS. 1 and 2, the outer tubular member 151 includes an opening 155 in a radial segment near the distal tip of the outer tubular member 151 through which the cutter 153 is configured to cut. The opening 155 and such openings of other embodiments are not required to have any specific shape but may be any effective shape through which cutting may be accomplished. More particularly, the inner tube or inner tubular member 152 is sized to fit within the outer tubular member 151 and be rotated relative to the outer tubular member 151. Because the outer tubular member 151 is rotationally fixed relative to the hub 110, 210, 310, changing orientation of the hub 110, 210, 310 relative to the drive unit 101, 201, 301 causes the opening 155 to be oriented at a changed orientation with the drive unit 101, 201, 301. The inner tubular member 152 includes a drive tang or torque transfer element 156 (FIGS. 2, 5C, 5D, and 8-10) configured to engage with and be turned by the drive unit 101, 201, 301. The torque transfer element 156 extends from a proximal end of the inner tubular member 152 to enable the inner tubular member 152 to be turned by the drive unit 101, 201, 301 when the hub 110, 210, 310 is seated in the drive unit 101, 201, 301, as shown in FIGS. 1, 5A, 6, and 11. Any effective mechanism for transferring torque from a drive unit to an inner tubular member may be used in other embodiments. The tubular configuration of the inner tubular member 152 may be useful in removing material cut or otherwise manipulated by a cutting tool by applying a negative pressure to the pathway within the inner tubular member 152. However, other embodiments may include an inner member that is not open along all or even part of its length.

The cutter 153 (FIG. 4) may include a sharpened edge that slices tissue directly and may include an edge that works in combination with an inner edge of the opening 155 to shear tissue between the inner tubular member 152 and the outer tubular member 151. A sharpened edge of some embodiments may be the same edge that shears tissue in combination with an outer component. The cutter 153 shown is integral with the distal end of the inner tubular member 152. In other embodiments, a cutter may be a module or component configured to couple at a distal end of the inner member by any effective mechanism. Cutting elements may be formed from the same material as an inner member or a different material. Cutting elements of various embodiments may include blades, burrs, rasps, abrasives, or any other devices effective to cut, abrade, scratch, rub, dislodge, or otherwise manipulate tissue.

Figure 11:
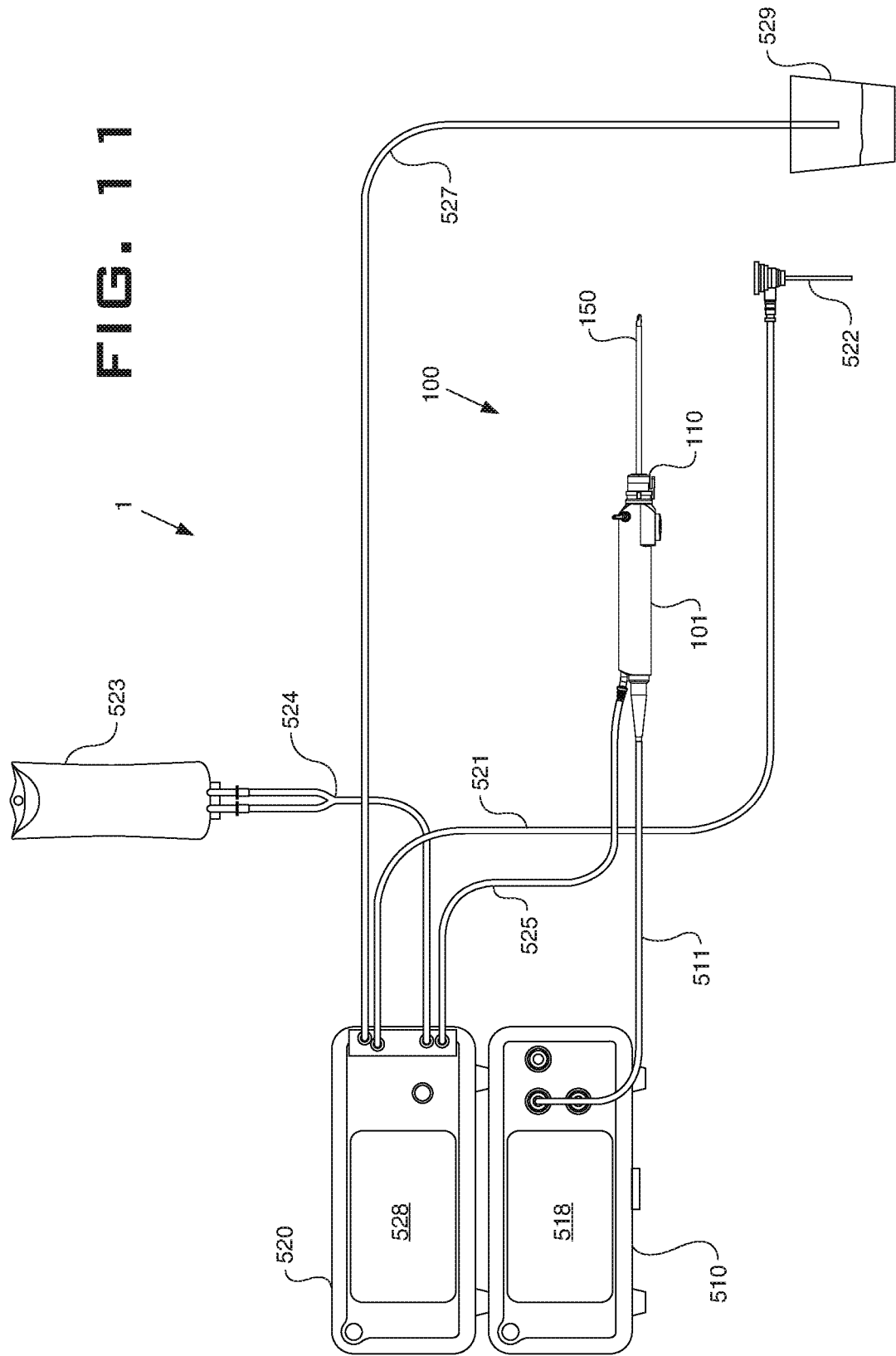
FIG. 11 is a system diagram of the cutting tool of FIG. 1 in combination with a control system for controlling use of the cutting tool and managing fluids.

Still another embodiment is a system for cutting 1 as illustrated in FIG. 11. The system for cutting 1 shown includes a cutting tool 100, a resection control 510, and a fluid management system. The cutting tool 100 is shown in FIG. 11, but either of the cutting tools 200, 300 or other alternative cutting tools may be employed as part of the system for cutting 1.

Embodiments of the depicted cutting tool 100 of the system for cutting 1 include the drive unit 101 with a longitudinal axis and a perimeter about a cross-section of the drive unit 101 transverse to the longitudinal axis, wherein there are multiple latch receiving locations in the form of an annular groove about the perimeter, a cutting implement 150 with a hub 110 configured to releasably couple with the drive unit 101, a latch configured to releasably couple between the hub 110 and at least one of the multiple latch receiving locations, and a cutter near a distal tip of the cutting implement 150.

The illustrated system for cutting 1 includes the resection control 510 that is electrically coupled with the drive unit 101 by a cable 511. The resection control 510 may be used to one or more of provide power to the drive unit 101, receive operator inputs from the drive unit 101, sense operating parameters of the drive unit 101, receive operator inputs from external switches or controls such as foot operated switches or controls, provide, set, or display alerts to a user based on operations of the cutting tool 100, and send and receive signals to and from a pump control 520. The resection control 510 illustrated also includes a resection display panel 518, which may be used to communicate information to a user and may be used to input settings or other information into the resection control 510 or other connected components of the control system. Other knobs, switches, controls, and the like may be used to control, set, or calibrate the resection control 510 as well.

In the illustrated embodiment, the pump control 520 is part of a fluid management system used in conjunction with fluid supply, tubing, and disposal components as described herein to facilitate the use of the cutting tool 100. For example and without limitation, fluids such as saline may be used during endoscopic surgical procedures to provide a clear operating medium in which to perform endoscopic surgical tasks. The pump control 520 may be used to one or more of provide fluid to the drive unit 101, sense operating parameters of the drive unit 101, manage waste fluid, receive operator inputs from external switches or controls such as foot operated switches or controls, and send and receive signals to and from the resection control 510. A fluid inflow line 521 is shown coupled between the pump control 520 and a patient joint cannula 522. The patient joint cannula 522 may provide one or both a passageway through which the cutting tool 100 may be introduced into a joint and an entry port for fluid supplied though the fluid inflow line 521. In other embodiments, one or more additional fluid lines may be used to supply fluid or remove fluid from a surgical site from locations different than those illustrated. A saline bag 523 is shown providing a fresh fluid supply to the pump control 520 through a supply line 524 in the present embodiment. Any other effective fluid source may be used in various embodiments. A suction line 525 is shown coupled between the cutting tool 100 and the pump control 520, which when activated draws waste fluid through the cutting tool 100 and into the pump control 520 where the fluid may be diverted for waste removal. A waste line 527 is shown coupled between the pump control 520 and a waste receptacle 529. Any other effective supply or waste handling mechanisms may be used in other embodiments. The pump control 520 illustrated also includes a pump control display panel 528, which may be used to communicate information to a user and may be used to input settings or other information into the pump control 520 or other connected components of the control system. Other knobs, switches, controls, and the like may be used to control, set, or calibrate the pump control 520 as well.

Various embodiments of a system wholly or its components individually may be made from any biocompatible material. For example and without limitation, biocompatible materials may include in whole or in part: non-reinforced polymers, reinforced polymers, metals, ceramics, adhesives, reinforced adhesives, and combinations of these materials. Reinforcing of polymers may be accomplished with carbon, metal, or glass or any other effective material. Examples of biocompatible polymer materials include polyamide base resins, polyethylene, Ultra High Molecular Weight (UHMW) polyethylene, low density polyethylene, polymethylmethacrylate (PMMA), polyetheretherketone (PEEK), polyetherketoneketone (PEKK), a polymeric hydroxyethylmethacrylate (PHEMA), and polyurethane, any of which may be reinforced. Polymers used as bearing surfaces in particular may in whole or in part include one or more of cross-linked and highly cross-linked polyethylene. Example biocompatible metals include stainless steel and other steel alloys, cobalt chrome alloys, zirconium, oxidized zirconium, tantalum, titanium, titanium alloys, titanium-nickel alloys such as Nitinol and other superelastic or shape-memory metal alloys.

Terms such as proximal, distal, near, around, and the like have been used relatively herein. However, such terms are not limited to specific coordinate orientations, distances, or sizes, but are used to describe relative positions referencing particular embodiments. Such terms are not generally limiting to the scope of the claims made herein. Any embodiment or feature of any section, portion, or any other component shown or particularly described in relation to various embodiments of similar sections, portions, or components herein may be interchangeably applied to any other similar embodiment or feature shown or described herein.

While embodiments of the invention have been illustrated and described in detail in the disclosure, the disclosure is to be considered as illustrative and not restrictive in character. All changes and modifications that come within the spirit of the invention are to be considered within the scope of the disclosure.

What is claimed is:
1. A system comprising:
a drive unit comprising:
  a longitudinal axis;
  a perimeter about a cross-section of the drive unit transverse to the longitudinal axis, the perimeter at a distal end of the drive unit;
  an annular groove disposed proximally of the perimeter on an outside surface of the drive unit;
  an opening at the distal end of the drive unit, the opening defines an internal volume with an inside surface; and
  two or more slots extending along the longitudinal axis and radially through the drive unit to the internal volume and open on the distal end of the drive unit;
a cutting implement comprising:
  a hub telescoped within the internal volume, an outside surface of the hub abuts the inside surface of the opening;
  one or more protrusions extending radially outward from the hub, at least one of the one or more protrusions telescoped with one of the two or more slots of the drive unit;

a latch disposed on the outside surface of the hub, the latch comprising an engaging member releasably coupled to the annular groove;
an outer tube coupled to the hub; and
a cutter near a distal tip of the outer tube.

2. The system of claim 1 wherein the two or more slots includes two slots and the one or more protrusions includes two protrusions corresponding to the two slots and each configured to be received in one of the two slots.

3. The system of claim 1 wherein the two or more slots includes three slots and the one or more protrusions includes three protrusions corresponding to the three slots and each configured to be received in one of the three slots.

4. The system of claim 1 wherein the latch further comprises:
a chamfered leading edge on a proximal end of the latch, the chamfered leading edge in operational relationship to the engaging member; and
the chamfered leading edge and engaging member configured such that when the hub is moved proximally along the longitudinal axis, the latch is forced into a position where the engaging member couples to the annular groove.

5. The system of claim 1 wherein the perimeter is circular at the cross-section.

6. The system of claim 1 wherein the latch further comprises a hinge that defines a rotational axis, and wherein the rotational axis, projected onto the longitudinal axis of the drive unit, is perpendicular to the longitudinal axis of the drive unit.

7. The system of claim 1 wherein a rotational axis of the latch is at least one selected from the group consisting of: tangent to the outside surface of the hub; and parallel to a tangent to the outside surface of the hub.

8. The system of claim 1 wherein the drive unit further includes a rim immediately adjacent the distal end of the drive unit, the rim extending radially outwardly from the longitudinal axis to form the annular groove and define the perimeter.

9. A cutting implement for use with a drive unit, the cutting implement comprising:
a hub that defines an outside surface;
an outer tube rigidly coupled to the hub, the outer tube defines a longitudinal axis;
an inner tube telescoped with the outer tube along the longitudinal axis;
a first protrusion that extends radially outward from the hub;
a latch disposed on the outside surface of the hub, the latch comprising:
an engaging member on an inside surface of the latch,
a chamfered edge on a proximal end of the latch, the chamfered edge in operational relationship to the engaging member, and
the chamfered edge and engaging member configured such that when the hub is moved proximally along the longitudinal axis, the latch is forced into a position where the engaging member couples to an annular groove of the drive unit; and
a cutter defined at a distal end of the outer tube and inner tube.

10. The cutting implement of claim 9 wherein the hub further comprises a second protrusion opposite the first protrusion on the outside surface of the hub.

11. The cutting implement of claim 9 wherein the hub further comprises a second protrusion that extends radially outward from the hub, and a third protrusion that extends radially outward from the hub, the first, second, and third protrusions disposed at equally spaced circumferential positions around a circumference of the hub.

12. The cutting implement of claim 9 wherein the latch resides between two protrusions along a circumference of the outside surface of the hub.

13. The cutting implement of claim 9 wherein the latch further comprises a hinge that defines a rotational axis, and wherein the rotational axis, projected onto the longitudinal axis, is perpendicular to the longitudinal axis.

14. The cutting implement of claim 9 wherein a rotational axis of the latch is at least one selected from the group consisting of: tangent to the outside surface of the hub; and parallel to a tangent to the outside surface of the hub.

15. A method comprising:
rotationally aligning a cutting implement such that one or more protrusions extending radially outward from a hub of the cutting implement align with at least one of two or more respective notches defined in a distal end of a drive unit, the two or more respective notches extending along a longitudinal axis of the drive unit and radially through the drive unit; and then
telescoping the hub of the cutting implement into an opening at the distal end of the drive unit; and simultaneously
telescoping the one or more protrusions into the at least one of the one of two or more respective notches;
latching the cutting implement to an annular groove defined on an outside surface of the distal end of the drive unit, the latching by a latch disposed on an outside surface of the hub; and
resecting tissue with the cutting implement and the drive unit.

16. The method of claim 15 wherein the two or more respective notches includes three respective notches and the one or more protrusions includes three protrusions corresponding to the three respective notches and each of the three protrusions is configured to be received in one of the three respective notches.

17. The method of claim 15 wherein latching further comprises:
rotating the latch in a first direction by a chamfered edge engaging a perimeter at the distal end of the drive unit, the rotating about a hinge axis of the latch; and then
rotating the latch in a second direction opposite the first direction about the hinge axis, rotation of the hinge in the second direction couples an engaging member within the annular groove on the distal end of the perimeter.

* * * * *